United States Patent
Gharib

(10) Patent No.: US 6,582,208 B2
(45) Date of Patent: Jun. 24, 2003

(54) BLADELESS PUMP

(75) Inventor: Morteza Gharib, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/917,094

(22) Filed: Jul. 26, 2001

(65) Prior Publication Data

US 2002/0044867 A1 Apr. 18, 2002

Related U.S. Application Data

(62) Division of application No. 09/557,277, filed on Apr. 24, 2000.
(60) Provisional application No. 60/140,897, filed on Jun. 23, 1999.

(51) Int. Cl.[7] ............... F04B 17/00; F04B 35/04
(52) U.S. Cl. ................. 417/423.1; 417/53
(58) Field of Search ............... 417/423.1, 53; 604/151, 152, 153

(56) References Cited

U.S. PATENT DOCUMENTS

| | | | |
|---|---|---|---|
| 3,017,848 A | | 1/1962 | Bishop ............ 115/16 |
| 3,738,773 A | | 6/1973 | Tinker ............ 416/179 |
| 3,977,976 A | * | 8/1976 | Spaan et al. ........ 210/321.68 |
| 5,088,899 A | * | 2/1992 | Blecker et al. ...... 417/356 |
| 5,254,248 A | * | 10/1993 | Nakamura .......... 310/321.67 |
| 5,507,629 A | | 4/1996 | Jarvik ............ 417/423.3 |
| 5,900,142 A | * | 5/1999 | Maloney et al. ..... 210/179 |

* cited by examiner

Primary Examiner—Charles G. Freay
Assistant Examiner—William H. Rodriguez
(74) Attorney, Agent, or Firm—Fish & Richardson P.C.

(57) ABSTRACT

A bladeless pump is made with rotating parts that are substantially flexible, allowing them to be assembled into desired shapes. The rotating part preferably has no blades thereon, and rotates to produce a fluid flow inside a chamber. The fluid flow in the chamber causes flow along the chamber axis, which itself may be bent.

12 Claims, 3 Drawing Sheets

BLADELESS PUMP

CROSS REFERENCE TO RELATED APPLICATIONS

This application is a divisional of U.S. application Ser. No. 09/557,277, filed Apr. 24, 2000 (pending), which claims the benefit of the U.S. Provisional Application No. 60/140,897, filed on Jun. 23, 1999, both of which are incorporated herein by reference.

FIELD OF INVENTION

The present application relates to a pump which is formed of rotating parts, which can operate without blades.

BACKGROUND

Rotating pumps often use blades or propellers to press a fluid in a desired direction. These blades can subject the liquids to harsh impact.

For instance, if the pump is used to pump blood, then the blades can actually cut or otherwise damage certain blood cells, resulting in hemalysis injuring the blood. In other cases, the blades can cause cavitation and produce undesired gas bubble turbulence in the fluid.

SUMMARY

The present application teaches a bladeless pump for fluid flow. While the pump has many different applications, one application of the pump is for use in pumping blood and other multiphase flows of body fluids. Other uses include thrust generation and propulsion.

One aspect of the application discloses a pump with a moving part that has a substantially smooth outer surface.

Other aspects include that outer surface having a substantially constant outer diameter. The moving part can be a rotating shaft held captive within an outer cylinder. The inside surface of the outer cylinder includes ridges thereon which are tilted a specified angle. The optimum angle is believed to be 45 degrees. However, any angle a, between (0<a>90 degrees) can produce a pumping effect.

A specified relatively small distance is maintained between the rotating substantially smooth inner surface, and the inside of the outer shell. This small distance can preferably be an amount that prevents substantial leakage of fluid between the ridges.

BRIEF DESCRIPTION OF THE DRAWINGS

These and other aspects will now be described in detail with respect to the accompanying drawings, wherein.

DETAILED DESCRIPTION

Figure 1:
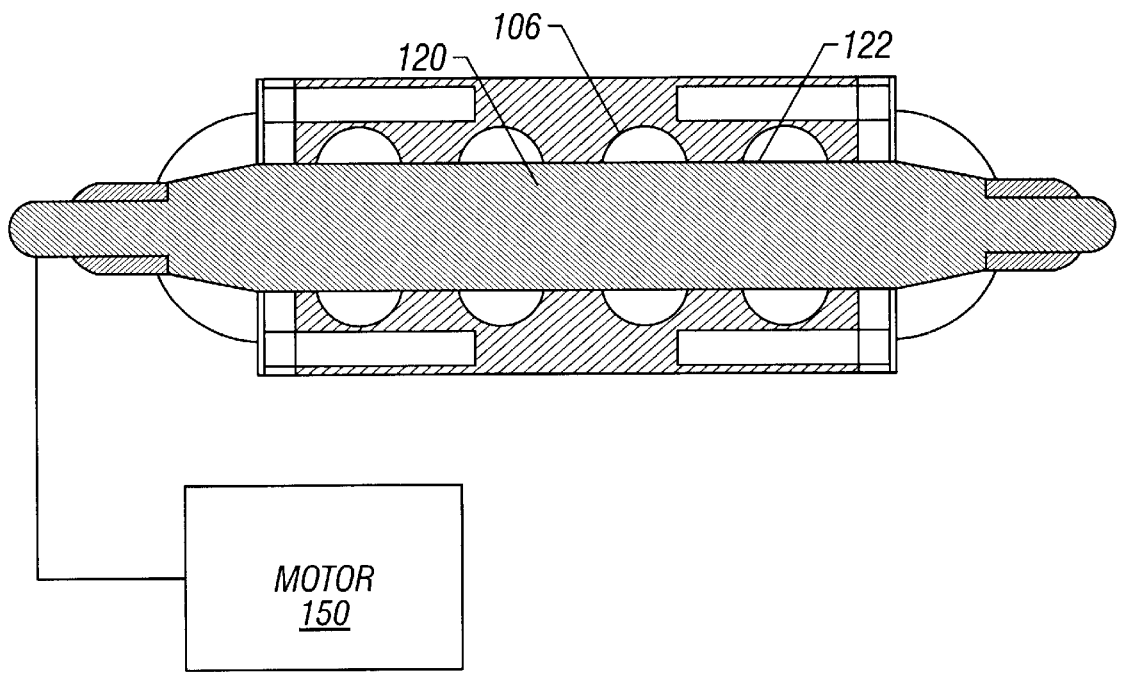
FIGS. 1–3 show different views of the pump from different angles.
Figure 2:
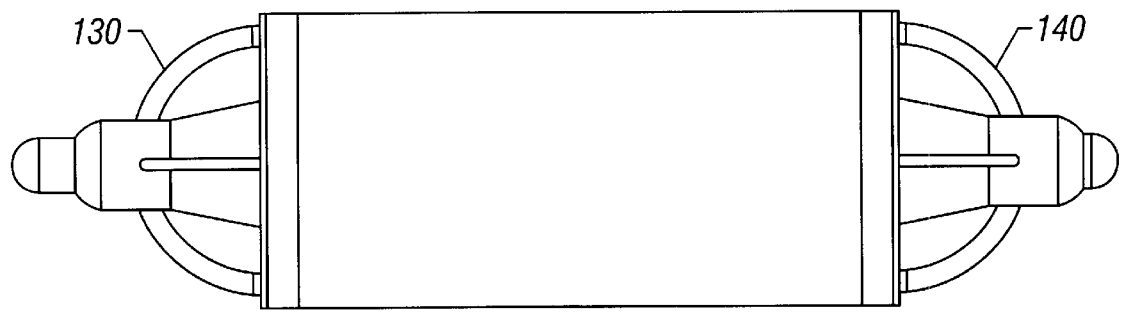
Figure 3:
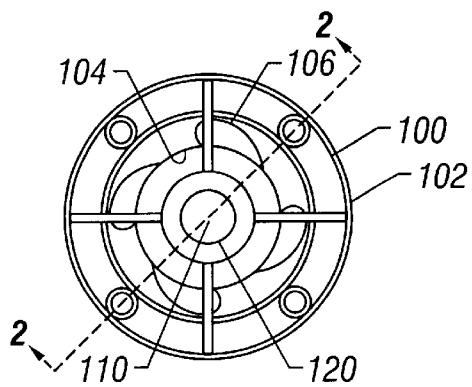

FIGS. 1 through 3 show different views of the pump of this embodiment. The pump is formed of two coaxial cylinders, one rotating within the other. An outer cylindrical housing 100 includes an outer surface 102 which can be of any desired size or shape. The inner surface 104 of the outer housing is formed with spirally-patterned grooves 106 thereon. The central axis 110 of the outer housing 100 defines a direction of fluid pumping.

A fluid pumping element 120 is located coaxially with the central axis 110. The fluid pumping element 120 has a substantially smooth outer surface 122. It preferably has no blades thereon. Blades, as that term is used herein, are sharp edged objects, such as the usual fan-shaped parts that are used in a pump.

In one embodiment, the fluid pumping element 120 is cylindrical and has a substantially constant outer diameter over its entire active surface. That constant outer diameter can be constant within 1 to 5 percent. The fluid pumping element can be a solid element, or can be a hollow element, such as a tube.

The pumping is held rotatably at its two ends by a first shaft holder 130 and a second shaft holder 140. The shaft can rotate within the first and second shaft holders. An electric motor 150 can provide rotational force to the end.

The inner surface of the outer shell defines a chamber includes a plurality of grooves on inner surfaces of the chamber. The inner surface can have a diameter of ID, which can range from sizes for operation to pump microfluidics ranging to a size fro submarine propulsion. The grooves are canted at a specified angle. Each of the grooves extends inward from the inner surface by a depth proportional to (OD–ID). The grooves are canted in the direction of desired rotation of the central shaft and in the direction of desired pumping. The pumping element can be rotated in the opposite direction to pump the fluid in the opposite direction.

The smooth inner cylinder 120 preferably has an outer diameter of ID–2 g, where g is the gap between the inner cylinder and the inner surface. The cylinder can also have smooth nose and ramp portions.

In operation, the central shaft is rotated in the specified direction at a specified rpm rate, e.g. between 5,000 and 20,000 rpm. A shearing force is produced proportional to the angular velocity of the inner cylinder diameter of the inner cylinder. The momentum is transferred to the rest of the fluid. This causes a laminar or turbulent flow around the shaft and along the shaft/groove axis. The viscose or turbulent shear flow eventually extends outward to the grooves.

The angular momentum of the fluid in the grooves has a vector component along its axis, forcing the fluid to move.

The grooves are preferably spaced by a maximum distance of one quarter the shaft diameter. However, there is no minimum effective minimum distance for the groove spacing. A typical groove pattern is usually canted by approximately 45 degrees relative to the direction of the central axis.

In operation, when the shaft spins, it causes a shearing laminar or turbulent flow around the shaft, thereby causing the fluid to flow outward. The shaft is close enough to the grooves to cause fluid flow in the grooves, and to prevent substantial leakage between the grooves.

The grooves facilitate the fluid flow movement. A particularly advantageous use of this pump is in blood flow. A known shear thinning effect in blood causes the red cells to avoid the high shear regions. The cells distance themselves from the high speed-rotating shaft and leave the plasma near the rotating shaft. This process does not occur instantaneously. However, in this pump, the approaching red blood cells feel the stagnation region of the smooth-surfaced rotating shaft. They cells then start an avoidance process with enough lead-time on a viscose time scale to avoid intersecting the path. Previous pumps that rely on the displacement action of the blades at high angular frequencies and speeds often do not leave enough response time for the red blood cells to avoid impact, and its subsequent damaging effects.

The present application pumps the red blood cells without using blades. Hence, there are no blades to cut into blood cells. The shear thinning effect causes the cells to stay away from the high shear portions. The grooves that are used can also be rounded to minimize any damage that could be caused to the blood cells by those grooves.

Many modifications are possible. As disclosed above, the device can be made in a number of different sizes, and the internal ridges can have a number of different sizes and shapes. The area between the internal ridges can be either edged or smooth.

The central shaft is preferably a constant diameter cylindrical rod. However, the shaft can alternatively be a varied diameter cylindrical rod or any other element that is smooth and does not include sharp edges thereon. For example, the cylindrical rod could be formed with an outer surface that has bumps that rounded edges.

Figure 4A:
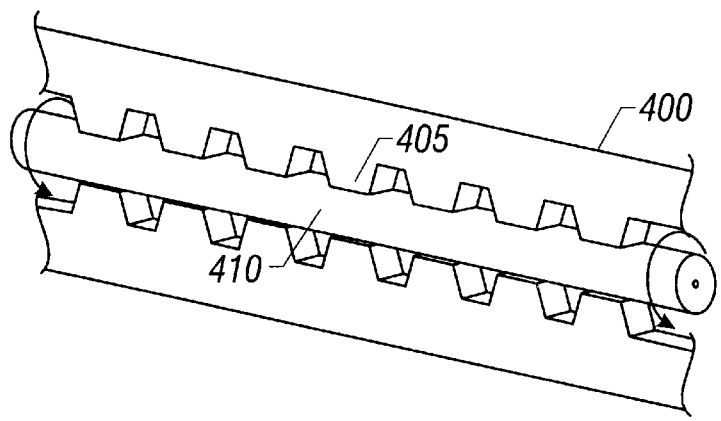
FIGS. 4A and 4B show flexible pumps.
Figure 4B:
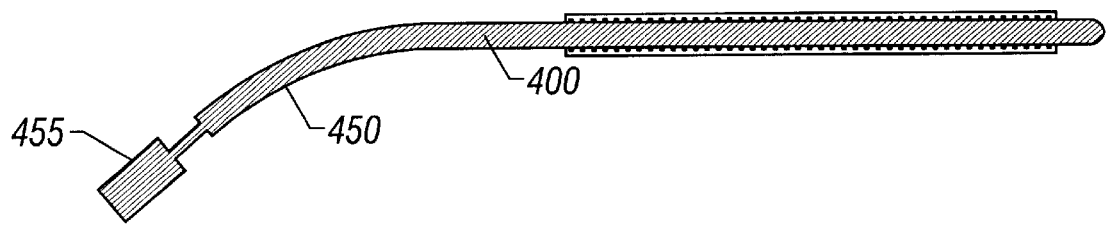

The way that the pump works allows other advantages. No sharp corner blades are used. Hence, the whole assembly can be made with flexible materials. One embodiment shown in FIG. 4 uses flexible tube 400 with inner grooves 405. A flexible cylindrical shaft or rod 410 rotates within the outer tube. This can be used for applications where local suction or blowing in complex inner cavities would be required. Another alternative shown in FIG. 4B forms the inner rotating part 400 from a flexible material; so that it can be bent at the area 450 to attach the driving motor.

A rotary motor 450 or any other kind of motor can carry out the rotation of any of these embodiments. One embodiment uses a magnetic levitation pump principle. According to this embodiment, the central shaft is made of a magnetic material. An external coil will generates magnetic field, and the external magnetic field causes the internal cylinder to rotate. The rotating cylinder causes the fluid flow as described above.

Figure 5:
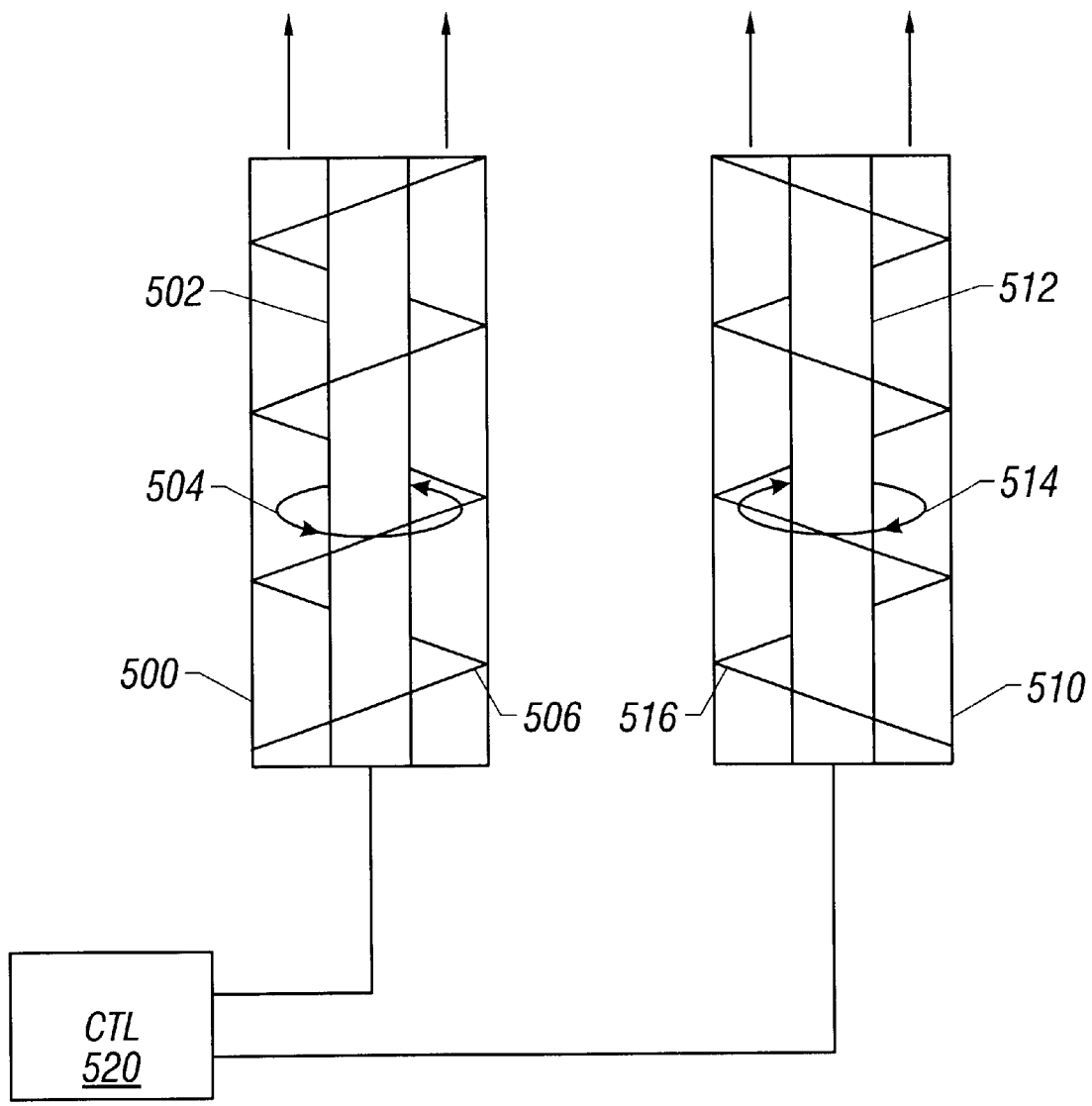
FIG. 5 shows a propulsion system.

One embodiment is for use in propulsion, e.g., as a motor to drive a water vehicle such as a submarine. This embodiment is shown in FIG. 5 with two propulsion pumps 500, 510 with rotating elements 502, 512 that rotate in opposite directions 504, 514. The cylinders have oppositely canted ridges 506, 510 so that they both pump in the same direction. This allows balance in the thrust generation. A control element 520 enables setting the rotating speed of each element individually. The thrust vector, caused when one of these moves faster than the other, can be used for maneuvering. For example, the left side pump part 500 can be initiated to pump faster than the right side pump part 510 to move in a more rightward direction.

This system has advantages when used for propulsion, e.g. thrust generation. The resulting system can be relatively quiet, since no blades cut the water.

This system also has advantages when used for pumping other materials that should not be damaged, besides blood. For instance, since an embodiment can be used which has no moving edges, this system can be used for pumping live aquatic animals or other damageable materials.

Other modifications are contemplated.

What is claimed is:

1. A flexible pump, comprising;
   a shaft, formed of a flexible material, and formed without blades thereon;
   a chamber, surrounding said shaft, and formed with grooves on an inner surface thereof facing an outer surface of said shaft, said grooves canted in a direction of desired fluid flow relative to a direction of desired rotation of said shaft; and
   a rotation receiving element, receiving rotary thrust, and operating to rotate said shaft relative to said second element.

2. A pump as in claim 1, wherein each of said shaft and chamber comprise hollow flexible tubes.

3. A pump as in claim 1, wherein said chamber comprises a hollow flexible tube.

4. A bladeless pump, comprising:
   a rotating part, which has no blades thereon and which rotates to produce a fluid flow, wherein said rotating part is flexible, and an outer surface, surrounding said rotating part, said outer surface including grooves which are slanted at a specified angle.

5. The pump as in claim 4, wherein said grooves are spaced by a maximum distance of one-quarter a diameter of said rotating part.

6. The pump as in claims 4, further comprising a motor element which rotates said rotating part.

7. The pump as in claim 6, wherein said rotating part is curved in an area that connects to said motor element.

8. A bladeless pump, comprising;
   a rotating part, which has no blades thereon and which rotates to produce a fluid flow, wherein said outer surface is substantially curved.

9. A pump, comprising:
   a shaft, which is rotatably mounted to rotate around a rotation axis, and which has substantially smooth outer surfaces; and
   a chamber surface, surrounding said shaft and having an inlet and outlet, wherein each of said shaft and said chamber surface are flexible, wherein said shaft and said chamber surface are each substantially curved.

10. A pump, comprising:
    a shaft, which is rotatably mounted to rotate around a rotation axis, and which has substantially smooth outer surfaces; and
    a chamber surface, surrounding said shaft and having an inlet and outlet, wherein each of said shaft and said chamber surface are flexible, wherein said first element has a curved portion, and said chamber surface is substantially straight.

11. A flexible pump, comprising:
    a shaft, formed of a flexible material, and formed without blades thereon;
    a chamber, surrounding said shaft, and formed with grooves on an inner surface thereof facing an outer surface of said shaft, said grooves canted in a direction of desired fluid flow relative to a direction of desired rotation of said shaft; and
    a rotation receiving element, receiving rotary thrust, and operating to rotate said shaft relative to said second element, wherein said first element and said second element are substantially curved.

12. A flexible pump, comprising:
    a shaft, formed of a flexible material, and formed without blades thereon;
    a chamber, surrounding said shaft, and formed with grooves on an inner surface thereof facing an outer surface of said shaft, said grooves canted in a direction of desired fluid flow relative to a direction of desired rotation of said shaft; and
    a rotation receiving element, receiving rotary thrust, and operating to rotate said shaft relative to said second element, wherein said first element and said second element are substantially straight over an area of intersection therebetween, and said first element has a curved portion thereon in a location adjacent said rotation receiving element.

* * * * *